United States Patent [19]

Neville

[11] Patent Number: 4,510,808
[45] Date of Patent: Apr. 16, 1985

[54] APPARATUS FOR THE CONTINUOUS MEASUREMENT OF BULK DENSITY MATERIAL SUCH AS CUT TOBACCO

[75] Inventor: Richard E. G. Neville, Salisbury, England

[73] Assignee: AMF Incorporated, White Plains, N.Y.

[21] Appl. No.: 498,354

[22] Filed: May 26, 1983

[30] Foreign Application Priority Data

Jun. 2, 1982 [GB] United Kingdom ............. 8216028

[51] Int. Cl.³ ............................................. G01N 9/02
[52] U.S. Cl. ......................................... 73/433; 177/121
[58] Field of Search ............... 73/433, 434, 435, 32 R; 177/50, 121

[56] References Cited

U.S. PATENT DOCUMENTS 4,170,251 10/1979 Hine ...................................... 177/50

FOREIGN PATENT DOCUMENTS 2250435 5/1975 France ................................. 73/433
308304 5/1972 U.S.S.R. .............................. 73/32 R Primary Examiner—James J. Gill
Attorney, Agent, or Firm—David E. Dougherty; Thomas J. Durling

[57] ABSTRACT

An apparatus is provided for the continuous measurement of the bulk density of particulate material comprising an endless belt weighing conveyor having a compression zone and a weigh span downstream of the compression zone, means for feeding the material to said compression zone, a compression unit at said compression zone having a series of rollers an axes extending transverse to the direction of movement of the weighing conveyor, and transducer means provided at the weigh span for producing signals proportional to material weight. The rollers may be driven with a surface speed equal to the weighing conveyor belt speed and additional rollers may be mounted below the weighing conveyor to carry the load. The rollers are preferably embraced by a belt which gives a continuous surface and prevents tobacco getting between the rollers. In which case, the belt is driven with the same speed as the weighing conveyor belt, via a terminal roller and the other rollers follow.

11 Claims, 2 Drawing Figures

APPARATUS FOR THE CONTINUOUS MEASUREMENT OF BULK DENSITY MATERIAL SUCH AS CUT TOBACCO

BACKGROUND TO THE INVENTION

This invention relates to apparatus for the continuous measurement of the bulk density of particulate material, more particularly cut tobacco.

STATEMENT OF PRIOR ART

UK Pat. No. 1,495,752 discloses a method for the continuous measurement of the bulk density of tobacco by means of a variable speed weighing conveyor and rectangular column feed, with the two larger walls formed by conveyor belts driven at the same speed as the weighing conveyor belt.

An alternative form of column was described with smooth fixed walls and two pinch rolls at the outlet of the column driven with a surface speed equal to the weighing conveyor belt speed.

The specification of UK Pat. No. 1,495,752 includes reference to the laboratory cylinder volume method of measuring the bulk density of tobacco which is to measure the volume of a fixed weight of tobacco in a vertical cylinder after compression by a free falling piston of fixed weight for a fixed time.

The size of cylinder and weight of piston vary between manufacturers giving pressure from 1 to 3 psi, (7 to 21 kPa) the higher pressure being used with smaller diameter cylinders.

The bulk compresses at a diminishing rate and the time is selected to give a nearly static volume. The density achieved is typically 0.25 gm/cc (referred to as a cylinder volume of 4 cc/gm) and matches the density of a cigarette.

It is found in a particular apparatus with 1.5 psi pressure (10 kPa) and 5 minute compression time that 90% of the density is achieved in 30 secs.

For the continuous measurement described above, with a 16"×8" (400 mm×200 mm) column, a tobacco level controlled to 36" (900 mm) high and 2,200 lbs/hr (1000 kg/h) flow rate, the 'settling time' or time through the column is 25 secs. and the measured density only 0.11 gm/cc, (9 cc/gm cylinder volume).

The level in the column is held constant independent of flow rate by a level detector which controls the speed of the weighing conveyor belt to maintain the level. The pressure on the tobacco at the bottom of the column due to the 'head' of tobacco is less than 0.14 psi (1 kPa), ignoring friction.

However, after compensation for moisture content, temperature and settling time (belt speed), there is a correlation with the laboratory cylinder colume test.

OBJECT OF THE INVENTION

An object of the invention is to improve the method of continuous measurement of bulk density material as described in UK Pat. No. 1,495,752 by matching the laboratory test more nearly and achieving similar densities.

SUMMARY OF THE INVENTION

According to the invention there is provided an apparatus for the continuous measurement of the bulk density of particulate material comprising an endless belt weighing conveyor having a compression zone and a weigh span downstream of the compression zone, means for feeding the material to said compression zone, a compression unit at said compression zone having a series of rollers on axes extending transverse to the direction of movement of the weighing conveyor, and transducer means provided at the weigh span for producing signals proportional to material weight.

The series of rollers occupy a length of conveyor sufficient to give appreciable compression time, e.g., 3' (900 mm) in the above example gives 25 secs.

The rollers may be driven with a surface speed equal to the weighing conveyor belt speed and additional rollers may be mounted below the weighing conveyor to carry the load.

The rollers are preferably embraced by a belt which gives a continuous surface and prevents tobacco getting between the rollers. In which case, the belt is driven with the same speed as the weighing conveyor belt, via a terminal roller and the other rollers follow.

The rollers and belt are free to move between two side walls, which may be extensions of the column side walls and the same distance apart.

The end roller adjacent the weighing span may be connected to a position transducer so that its height above the weighing conveyor belt can be measured continuously.

Should the weight of the rollers or the belt be insufficient to give the pressure of 1 to 2 psi (7 to 14 kPa) required, which on 36" (900 mm) length×16" (400 mm) width amounts to a total load of 576 to 1152 lbs (262 to 524 kg), additional loading may be applied to each roller by springs or pneumatic cylinders with accurately controlled air pressure, or preferably bellows to remove friction.

Each roller may be mounted independently on a fixed carriage by arms or slides, so that pressure is applied uniformly for the length of the compression zone.

However, preferably it is simpler and adequate to fix the rollers to a carriage, which is free to move vertically as a whole, and apply four air cylinders to the carriage. This gives a consistent but not uniform pressure. A more uniform pressure can be achieved by arranging the rollers in a curved path to match the compression of the tobacco.

The carriage may be pivoted at the feed end and free to move vertically at the discharge end. This simplifies the drive but effectively halves the compression time.

Since the compression rollers and belt have to operate freely between side walls, the rollers may be divided to provide two internal bearing points and the belt fitted with internal vee belt guides which run in grooves in the rollers to maintain precise tracking. The band is of heavy gauge to provide support between the pressure rollers. Alternatively, a timing belt with flanged pulleys could be used.

The compression belt could be driven from the weighing conveyor by an articulated drive, but is more easily driven by a separate geared motor. If both the weighing conveyor and compression belt motors are synchronous, they can be driven at the same speed by a common variable frequency inverter.

Since it is difficult to spread tobacco uniformly over wide conveyors and wide columns, the system is less satisfactory with large throughputs. Since also it is desirable to have long settling and compression times, the system is best suited to low feed rates below 2,200 lbs/hr (1000 kg/h). So for high throughputs it is preferable therefore to make the measurement in a by-pass carrying a part of the total tobacco flow.

Since the tobacco is compressed to double the normal density for this stage of the process, it may be desirable to minimise the amount of tobacco in the by-pass. This could be achieved by lengthening the compression time and/or by miniaturising the equipment, e.g., for the 16"×8" column (400×200 mm), a compression time of 5 minutes would require a belt speed of approx. 7"/min. (3 mm/sec) and a tobacco flow of approx. 220 lbs/hr (100 kg/h) alternatively an 8"×4" (200 mm.×100 mm) column with 18" (450 mm) level, 18" (450 mm) compression zone, 18" (450 mm) weigh span and 1 min. compression time would require a flow of approx. 250 lbs/hr (110 kg/h).

In general, the larger equipment is easier to feed. A typical main flow is 10,000 lbs/hr (4500 kg/h) so 200 lbs/hr (115 kg/h) represents 2%. Removing this small proportion from the main flow as a representative sample is achieved by the diversionary chute, which diverts the whole flow for a short period of say 1 second every 50 seconds.

The resulting approximate 3 lb.(1.5 kg) portion is spread by a climbing vibrating conveyor and fed into the column over a period of approximately 5 seconds, where it occupies approximately 6" (150 mm) height.

Such a by-pass system has the advantage that the weighing conveyor, pinch rolls and compression belt can be run at constant speed and a single level control used in the column to demand a portion of tobacco each time it is uncovered, thus generating a constant volume flow.

BRIEF DESCRIPTION OF DRAWINGS

The invention will now be described by way of example with reference to the accompanying drawing in which.

DESCRIPTION OF PREFERRED EMBODIMENTS

Figure 1:
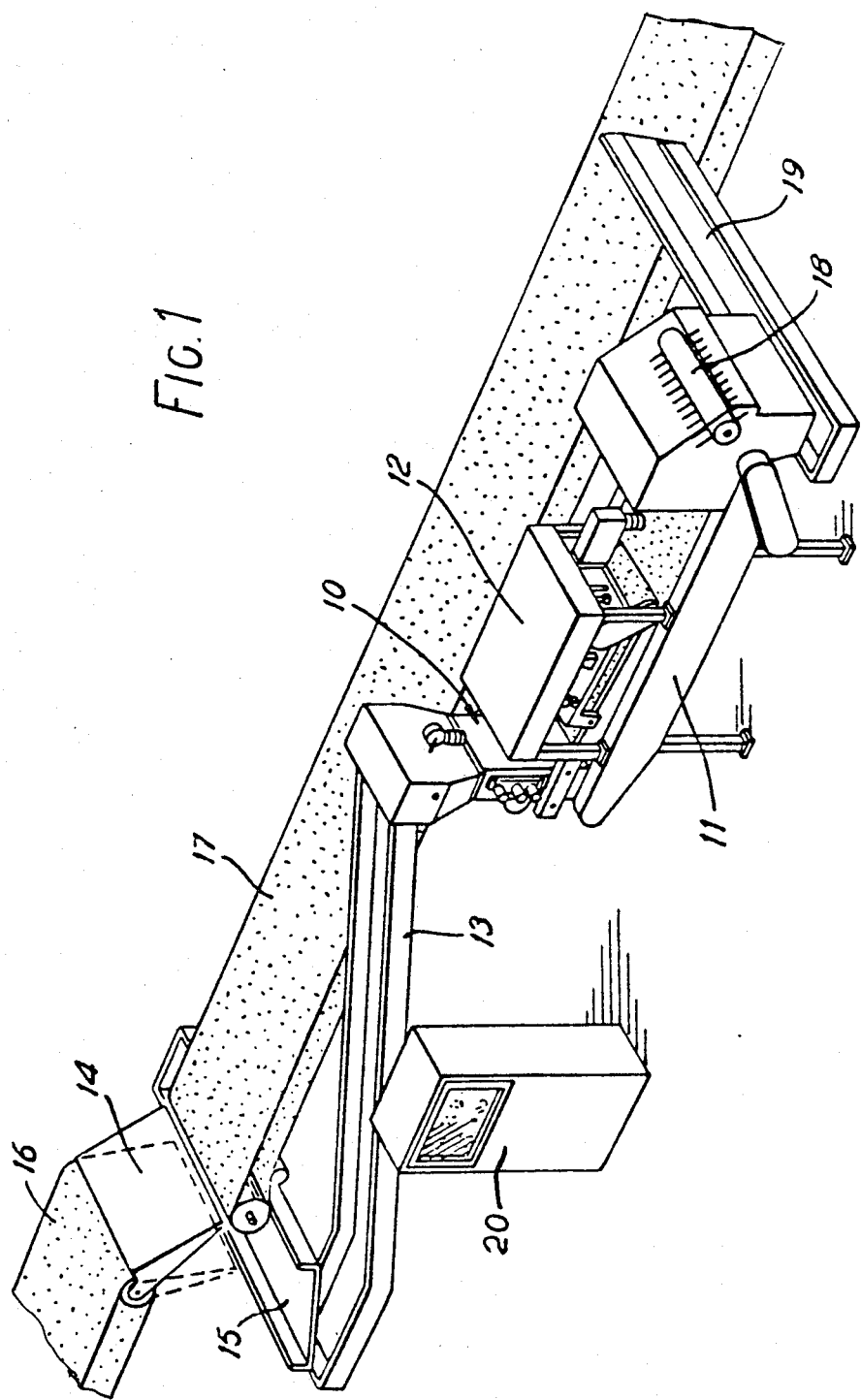
FIG. 1 is a perspective view of the apparatus for the continuous measurement of the density of a bulk of tobacco being conveyed.

The apparatus of the example described is designed to handle about 100 kg/h (220 lbs/hr) of cooled cut tobacco in a by-pass to the main flow and apply pressure up to 3 psi (21 kPa) for a period of 5 minutes to simulate the cylinder volume filling power measurement.

The machine runs at a fixed speed (except for emptying the system at the end of a run) and draws samples from the main flow as required to maintain a continuous flow through the measuring equipment.

The apparatus comprises a metering tube 10 disposed over one end of a weigher conveyor 11. Arranged above the weighing conveyor is a compression unit 12. The metering tube is fed by a vibratory conveyor 13 receiving samples of the main flow of tobacco to be continuously monitored by way of a diverter 14 and chute 15 disposed between two horizontally disposed conveyors 16, 17 conveying the tobacco to a maker, packer or storage location. The tobacco samples are returned from the discharge end of the weighing conveyor to the conveyor 16 by way of a doffer 18 and a delivery chute 19.

The various mechanical, pneumatic and electric actuators to be described later are controlled from a control cubicle 20.

The metering tube 10, rectangular in cross section preferably measuring 200×400 mm (8"×16"), is made of stainless steel sheet and provides a constant volume flow to the weighing conveyor and the compression unit 12.

Figure 2:
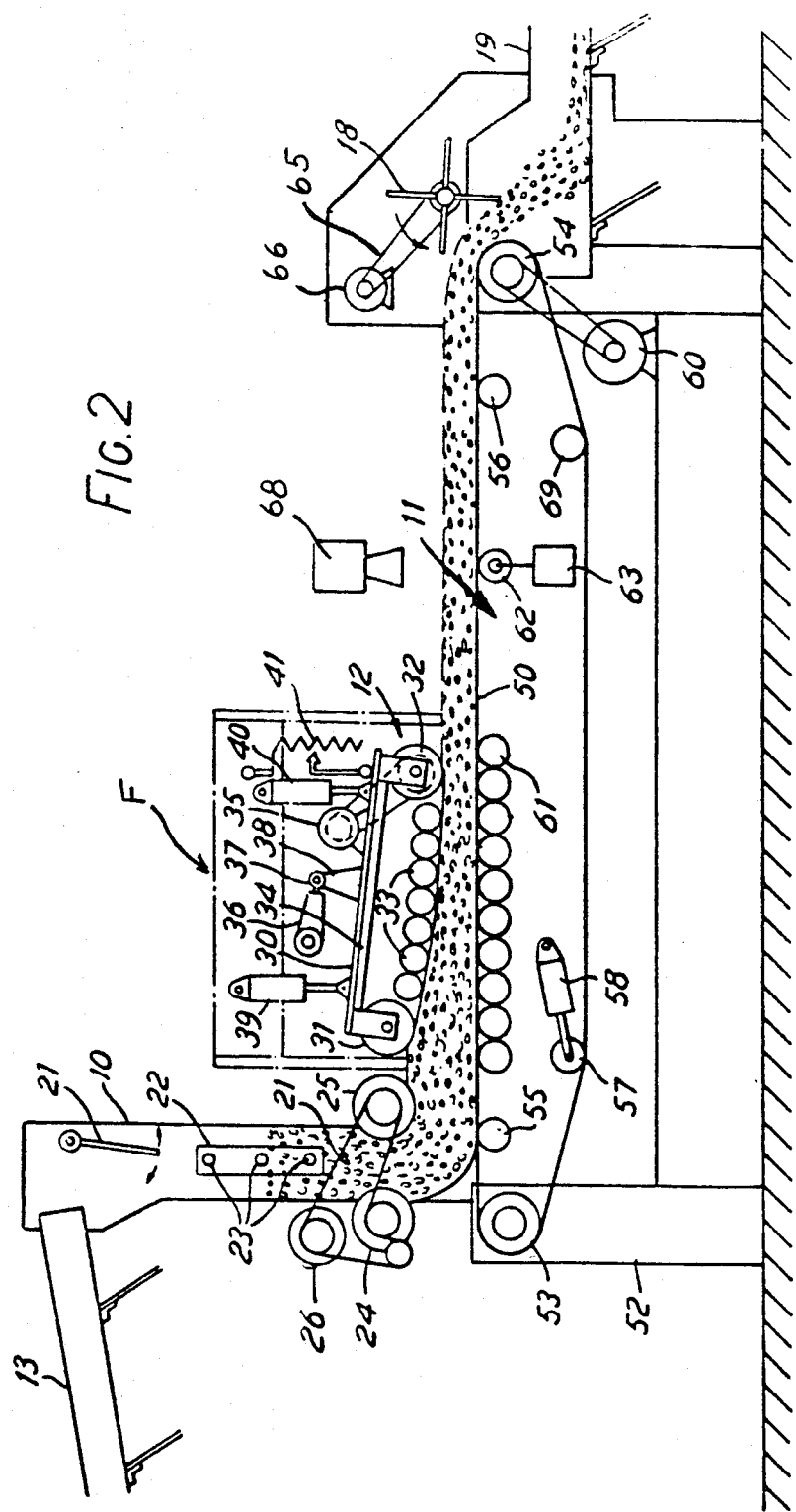
FIG. 2 is a schematic side elevation of a portion of the apparatus comprising the weighing conveyor, compression unit and metering tube.

The upper end of the tube 10 is fitted with an oscillating deflector 21 (see FIG. 2) powered by a 0.09 kW (⅛ hp) 60 rpm geared motor (not shown) to ensure uniform filling of the tube over the 200 mm (8") dimension.

Windows 22 are fitted in the tube sides with photo cell detectors 23 to control start up and diversion of tobacco from the main conveyor 17, 18.

A pair of pinch rolls 24, 25 driven by a 0.09 kW (⅛ hp) 3.3 rpm synchronous gear motor 26 to give the same surface speed as the weighing conveyor is fitted at the lower end of the tube 10 to ensure a steady flow onto the weighing conveyor 11.

Since the tobacco carpet on the weighing conveyor reflects the shape of the column, it is preferable to chamfer the outer corners of the column to prevent tobacco getting between the belt or rollers and the side walls.

A thermistor temperature sensor probe 21 projects into the tobacco stream at the base of the metering tube to measure tobacco temperature.

The compression unit 12, 760 mm (30") long 400 mm (16") wide comprises a carriage 30 with large diameter end rolls 31, 32 and a succession of smaller rollers 33 all embraced by an endless belt 34 with built in edge guides (not shown). The belt 34 is driven by a 0.09 kW (⅛ kW) 3.3 rpm synchronous geared motor 35 to give the same speed as the belt of the weighing conveyor.

The carriage 30 is supported above the weighing conveyor 11 from a framework shown generally at F by two link arms 36 connected by a torque tube 37 and two brackets 38, so that the carriage is free to move vertically.

The carriage floats on the surface of the tobacco between two fixed low friction side plates (high density polyethylene) not shown. Additional pressure in the range 1 to 3 psi (7 to 21 kPa) is applied by two low friction roller diaphragm air cylinders 39, 40 fed with air from a precision air set and gauge (not shown).

The thickness of the tobacco carpet at the delivery end roller of the compression unit is measured by a position transducer 41.

The weighing conveyor 11 comprises an endless weigh belt 50, 750 mm (30") wide carried from the conveyor support frames 52 by two end rolls 53, 54 disposed at 2550 mm (100") centres. The upper run of the belt passes over two spaced apart rollers 55, 56 on fixed axes. The lower run of the belt 50 passes over a tracking roller 57, controlled by a linear actuator 58, and a roller 69 on a fixed axis. The end roller 54 is driven at 160 mm/min (6.3"/min) from 0.09 kW (⅛ hp) 3.3 rpm synchronous geared motor 60. The weigh span, 760 mm (30") is defined by the end roller 61 of the series of rollers 61 on fixed axes extending beneath the compression unit and rollers 56. A weight sensing roller 62 is arranged midway between the roller 61 and roller 56 and is carried by a weigh beam (not shown) mounted on frictionless flexure pivots. The weight is sensed by a strain gauge type load cell 63.

The weigh belt 50 may be tracked automatically by a belt edge detector and steering roller in the return run of the belt.

The doffer 18 is adjustable in height and is driven by belt 65 from 0.09 kW 15 rpm geared motor 66 to assist in the opening of the compressed tobacco.

Belt travel speed is determined by an optical encoder on the shaft of the end roller 54 and is used to correct for the displacement of the carpet height and weight measurements.

An infra red moisture meter (e.g., Quadrabeam made by Moisture Systems Inc. Boston, Mass., USA) 66 is mounted on the framework over the weigh span.

A diverter 14 (see FIG. 1) in the main flow conveyor system enables 0.5 to 5 second samples to be removed according to flow rate, e.g., a 1 second sample from a 12,000 lb/hr flow rate is 3.3 lbs or approx. 150 mm. (6") in the metering tube.

The diversion chute enables samples of no more than 1.5 kg (3.3 lbs) to be removed from the main flow of tobacco. To be representative these samples must be a cross-section of the whole flow and not a sample from one side.

The vibrating conveyor 13 may be fitted with deflectors to spread the tobacco sample and ensure that the metering tube 10 is filled as uniformly as possible.

A sample is initiated by exposure of the photo cell level detectors 23 in the metering tube 10. The diverter 14 is then opened for a pre-set time. A further sample cannot be initiated until a further pre-set time has elapsed, which is greater than the time the sample takes to convey from the diverter to the tube.

The tobacco takes 20 minutes to pass through the equipment, so a speed-up by a factor of ×10 is provided to clear the equipment of tobacco at the end of a run.

To achieve this speed-up the pinch rollers 24, compression belt 34 and weigh belt 50 are all driven in synchronisation from a single 0–120 Hz variable frequency inverter with two preset output frequences. To empty the equipment at the end of a run in approx. 2 minutes the maximum high frequency of 120 Hz is selected.

For filling power measurement a lower frequency of 12 Hz is selected to give a compression time of 5 minutes and a flow rate of 220 lbs/hr (100 kg/h). The frequency of drive belt ratio can be adjusted to give shorter or longer compression times with corresponding flow rates.

The control cubicle 20 houses the motor switch gear, the filling power computation, level control timers and displays.

A microprocessor calculates the filling power as:

$$\frac{\text{Carpet width} \times \text{height} \times \text{weigh span}}{2 \times \text{weight on sensing roller}} \text{ ml/g (cc/gm)}$$

and makes correction for displacement of the weigh span relative to the carpet height, and also corrects for tobacco moisture content, temperature and belt speed (see UK Pat. No. 1495752).

The calculation is updated for every 3 mm. (⅛ in) belt travel and averaged for the previous 5, 10 or 20 minutes.

All the variables can be displayed digitally and a three pen chart recorder continuously records the filling power and any other two variables.

4–20 mA isolated signals are provided for each of the measured variables which are calibrated and displayed as follows:

| Weigh belt load cell | 0–2 lbs | (0–10 kg) |
|---|---|---|
| Carpet depth sensor | 2–6 ins | (50–150 mm) |
| Tobacco temp sensor | 50–150° C. | (10–60° C.) |
| Moisture meter | 10–20% | (10–20%) |
| Filling power | 20–120/10 g | (2–12 ml/g) |

The dead weight of the compression unit gives a pressure of 1 psi (0.07 kg/cm²) on the tobacco.

Additional pressure can be applied by the roller diaphragm air cylinders 39, 40 and is fixed by the precision air set. Each 35 psig (2.4 kg/cm²) of air pressure applies a further 1 psig (0.07 kg/cm²) to the tobacco. A precision air gauge calibrated up to 100 psig (7.0 kg/cm²) indicates the air pressure.

I claim:

1. An apparatus for the continuous measurement of the bulk density of particulate material comprising:
    a weighing conveyor having a compression zone and a weigh span downstream of the compression zone;
    means for feeding the material to said compression zone;
    a compression unit at said compression zone;
    a series of rollers in said compression unit disposed on axes extending traverse to the direction of movement of the weighing conveyor;
    transducer means provided at the weigh span for producing signals proportional to the material weight; and
    an endless belt embracing said series of rollers to provide a continuous surface adjacent to said weighing conveyor in the compression zone.

2. An apparatus according to claim 1 further comprising: a series of lower rollers provided beneath and in contact with the upper run of the weighing conveyor in the compression zone.

3. An apparatus according to claim 1, including a supporting framework and wherein the compression unit comprises a frame for supporting the rollers, said frame being suspended on the supporting framework above the weighing conveyor.

4. An apparatus according to claim 3, wherein a motor is mounted on said frame and serves to drive the belt at the same speed as the weighing conveyor.

5. An apparatus according to claim 3 or 4, wherein pneumatic cylinders are provided between the supporting framework and the frame to urge said compression unit towards said weighing conveyor.

6. An apparatus according to claim 1, wherein the axes of the rollers are disposed on a curved path.

7. An apparatus according to claim 1, wherein the rollers form with said weighing conveyor a space gradially decreasing in the direction of travel of the weighing conveyor.

8. An apparatus according to claim 1, wherein a position transducer is connected to said compression unit for indicating the thickness of the carpet of material at the outlet of the compression zone.

9. An apparatus as claimed in claim 1 wherein said feeding means comprises a vertical column, and further comprising: a series of pinch rollers at or near the lower end of the column and a motor to drive said pinch rollers at a peripheral speed equal to the speed of said weighing conveyor.

10. An apparatus according to claim 9, wherein an oscillatory arm is provided at the upper end of the column to effect even spread of the material entering the column.

11. A system for conveying particulate material and effecting continuous measurement of the bulk density of the material comprising;
(a) a first conveyor;
(b) a second conveyor for receiving the material from the first conveyor;
(c) a diverter arranged between said first and second conveyor, said diverter being movable from a first position in which it serves to bridge the two conveyors to a second position to divert a sample of the material;
(d) a third conveyor for receiving the samples from the diverter;
(e) an endless belt weighing conveyor disposed adjacent and parallel to said second conveyor, said weighing conveyor having a compression zone and a weigh span downstream of the compression zone;
(f) means for feeding the material to said compression zone;
(g) a fourth conveyor to deliver the sampled material to the feeding means;
(h) a compression unit at said compression zone having a series of rollers on axes extending transverse to the direction of movement of the weighing conveyor;
(i) transducer means provided at the weigh span for producing signals proportional to material weight;
(j) a doffer at the feed end of the weighing conveyor to open the compressed material after weighing; and
(k) a fifth conveyor for returning the opened material to the second conveyor.

* * * * *